United States Patent
Houmanfar et al.

(10) Patent No.: US 9,510,789 B2
(45) Date of Patent: Dec. 6, 2016

(54) MOTION ANALYSIS METHOD

(71) Applicants: Roshanak Houmanfar, Waterloo (CA); Michelle Elisabeth Karg, Kitchener (CA); Danica Kulic, Waterloo (CA)

(72) Inventors: Roshanak Houmanfar, Waterloo (CA); Michelle Elisabeth Karg, Kitchener (CA); Danica Kulic, Waterloo (CA)

(*) Notice: Subject to any disclaimer, the term of this patent is extended or adjusted under 35 U.S.C. 154(b) by 415 days.

(21) Appl. No.: 14/069,304

(22) Filed: Oct. 31, 2013

(65) Prior Publication Data
US 2015/0120016 A1    Apr. 30, 2015

(51) Int. Cl.
*G06F 19/00* (2011.01)
*A61B 5/00* (2006.01)
*A61B 5/11* (2006.01)

(52) U.S. Cl.
CPC ........... *A61B 5/7267* (2013.01); *A61B 5/1122* (2013.01); *A61B 5/725* (2013.01)

(58) Field of Classification Search
CPC  A63F 13/06; A63F 2300/105; G06F 19/3481; A61B 5/725; A61B 5/7267; A61B 5/1122

USPC ..................................................... 700/91, 92
See application file for complete search history.

(56) References Cited

U.S. PATENT DOCUMENTS

2011/0004126 A1* 1/2011 Einav ................. G06F 19/3481
600/595

* cited by examiner

*Primary Examiner* — Omkar Deodhar
*Assistant Examiner* — Wei Lee
(74) *Attorney, Agent, or Firm* — Venjuris, PC (57) ABSTRACT

The present invention relates to an automated system of measuring and assessing an individual's improvement in motion (for example, a patient's recovery) through exercise performance. In an embodiment of the system of the present invention, two approaches for monitoring movement are introduced for quantifying an individual's performance. Both approaches consider the control population as their reference and consider the difference, or what is referred to in this application as the distance, between the individual's data and the control population as the measure of performance.

4 Claims, 8 Drawing Sheets

(a) P2 knee extension

(b) P2 knee hip extension/Flexion

(c) P2 squat

(d) P18 knee extension

(e) P18 knee hip extension/Flexion

(f) P18 squat (g) P8 knee extension (h) P8 knee hip extension/Flexion (i) P8 squat

MOTION ANALYSIS METHOD

FIELD OF THE INVENTION

The present invention relates to an automated system of measuring and assessing physical mobility through exercise performance.

BACKGROUND

Mobility improvement for patients is one of the primary goals of physiotherapy rehabilitation. Providing the physiotherapist and the patient with a quantified and objective measure of progress can be beneficial for monitoring the patient's condition.

The application of machine learning techniques to human motion analysis has grown rapidly in recent years. Measurement and analysis of physiotherapy data has the potential to provide an objective and quantitative measure of a patient's progress and improvement in motion performance over the course of his or her physiotherapy treatment. During a typical physiotherapy session, a physiotherapist instructs the patient to perform a number of exercises, each with several repetitions. The set of exercises chosen and the number of repetitions may be customized for each patient. The physiotherapist then evaluates the patient's progress based on their performance. As the patient's condition improves the patient's performance also improves.

In current clinical practice, the patient's condition is typically assessed using visual observation of the patient's motions, questionnaires, and goniometry. Questionnaires such as the Community Balance and Mobility Scale and the Falls Efficiency Scale are used to assign a score to the patient's motion quality. Goniometry is a technique of measuring joint angles which isolates a single body joint in order to evaluate a subject's range of motion. Goniometry is not accurate when the subject is moving e.g., during exercises and functional rehabilitation.

The current measurement and assessment techniques require physiotherapist effort and monitoring, and are not capable of measuring during movement. Automation of patient observation would support physiotherapy practice through automated assessment and evaluation of exercise performance.

An automated system could also provide the therapist with numerical metrics to assess the patient's recovery process and potentially allow physiotherapists to assess the effectiveness of various treatment protocols over a population of patients.

Patient data analysis for progress monitoring is a challenging task because of the complexity of human motion. Human movement consists of synchronous recruitment of multiple degrees of freedom (DoF), making single DoF comparisons (e.g., only comparing the range of motion in one joint) incomplete and possibly unreliable. Furthermore there are many sources of variability in human motion data.

For a single individual performing several repetitions of the same movement, there is both spatial and temporal variability. This variability is due to the nature of human movement, each repetition of the same exercise will be different, due to the stochastic nature of muscle recruitment. Interpersonal variability is due to differences in the physical characteristics of different individuals, such as differences in height, weight, fitness level, etc. The measurement system, such as sensor noise and a gyroscope drift cause variability in the patient motion data. Initial pose and sensor positioning could introduce variability into patient data. Recovery and progress cause changes in the patient motion data over the course of treatment. As well, fatigue and tiredness over the course of a session can change movement characteristics.

The presence of multiple other sources of variability makes the task of progress monitoring challenging. It is therefore desirable to provide the patient and the therapist with objective quantified feedback. It is also desirable to provide other individuals with such feedback on mobility progress, for example, athletes or assembly-line workers.

SUMMARY OF THE INVENTION

In an embodiment of the present invention a system is provided in which a set of selected movements by an individual are measured over a period of repetitions and sessions and the individual's progress is also measured. In an embodiment of the system of the present invention, two approaches for monitoring patient movement are introduced for quantifying patient performance. Both approaches consider the healthy population as their reference and consider the difference, or what is referred to in this application as the distance, between the patient's data and the healthy population as the measure of performance. Distance measures are defined to capture the performance of one repetition of an exercise or multiple repetitions of the same exercise. To capture patient progress across multiple exercises, a quality measure and overall score are defined based on the distance measures and are used to quantify the overall performance for each session. In the examples illustrating the present invention, the effectiveness of these measures in detecting patients' progress is evaluated on rehabilitation data recorded from patients recovering from knee or hip replacement surgery. The measures of performance are able to capture the trend of patient improvement over the course of rehabilitation. The trend of improvement is not monotonic and differs between patients.

In an embodiment of the present invention there is provided a method for analysing an individual's motion through a computer programmed to process information, comprising the steps of:
  measuring control linear acceleration and angular velocity, using sensors on at least one control person performing a set of repetitions of an exercise;
  measuring individual linear acceleration and angular velocity, using sensors on said individual performing a set of repetitions of an exercise;
  inputting the measured control linear acceleration and angular velocity and individual linear acceleration and angular velocity into said computer to convert to joint angle positions, velocities and accelerations data for said individual and for said at least one control person;
  segmenting said data such that each segment begins with the start of an exercise repetition and ends when the exercise repetition is finished;
  extracting feature vectors from said data such that a control feature vector is $V'_H = V_H(\text{top}_{features})$ and an individual's feature vector is $V'_P = V_P(\text{top}_{features})$ and said top features differentiate the individual from the at least one control person;
  calculating a mean of the at least one control person's feature vector such that $\mu_H = \text{mean}(V'_H)$;
  calculating a diagonal matrix of standard deviations for the at least one control person's feature vector, such that $\Sigma_H = \text{diag}(\text{std}(V'_H))$;

and calculating a distance between one repetition of the exercise performed by said individual and the at least one control person's performance using $\delta_i = (V'_{Pi} - \mu_H)^T \Sigma_H (V'_{Pi} - \mu_H)$.

In an embodiment of the present invention there is provided a method for measuring quality of a repetition set of said exercise above, wherein $$Q_j = \frac{(\Delta_{Pj} \mu_{\delta Hj})}{\sigma^2_{\delta Hj}},$$

and j is said exercise, $\Delta_{Pj}$ is the individual's said distance measure for the repetition set of said exercise, $\mu_{\delta Hj}$ is the mean of the at least one control person's distance measure vector $\delta_{Hj}$, and $\sigma_{\delta Hj}$ is the standard deviation of the at least one control person's distance measure vector $\delta_{Hj}$.

In an embodiment of the present invention there is provided a method for measuring the score for a set of more than one of said exercises j above wherein the score is $$S = \sqrt{\sum_{\Omega \in \Gamma} \left( \frac{n_\Omega}{\sum_{\Omega \in \Gamma} n_\Omega} \frac{\mu_{d_{H\Omega}}}{\sigma^2_{d_{H\Omega}}} \right)^2} - \sqrt{\sum_{\Omega \in \Gamma} \left( \frac{n_\Omega}{\sum_{\Omega \in \Gamma} n_\Omega} Q_\Omega \right)^2}$$

where $\Gamma$ is said set of exercises, $\Omega$ is an exercise in the $\Gamma$, $n_\Omega$ is the number of repetitions for exercise $\Omega$, and $Q_\Omega$ is said quality measure of claim 2 calculated for exercise $\Omega$.

In an embodiment of the present invention there is provided a method for analysing an individual's motion through a computer programmed to process information, comprising the steps of:
  measuring linear acceleration and angular velocity, using sensors on at least one control person performing a set of repetitions of an exercise;
  measuring linear acceleration and angular velocity, using sensors on said individual performing a set of repetitions of an exercise;
  inputting the measured control linear acceleration and angular velocity and individual linear acceleration and angular velocity into said computer to convert to joint angle positions, velocities and accelerations data for said individual and for said at least one control person;
  segmenting said data such that each segment begins with the start of an exercise repetition and ends when the exercise repetition is finished;
  extracting feature vectors based on the exercise repetition from the at least one control person and said individual, wherein said features differentiate the individual from the at least one control person;
  determining the distance between at least one control person and said individual for that exercise repetition using the feature vectors,
  calculating the median of the exercise repetition for the at least one control person and calculating the median of the repetition set for the individual;
  calculating the quality of a repetition set of an exercise based on the individual's distance measure for each repetition set; and
  calculating the score of the exercise set based on the quality of each of said repetition sets.

In an embodiment of the present invention there is provided a computer-implemented method for selecting features which distinguish data collected from an individual from data collected from at least one control person comprising the steps of:
  measuring linear acceleration and angular velocity, using sensors on said at least one control person performing a set of repetitions of an exercise;
  measuring linear acceleration and angular velocity, using sensors on said individual performing a set of repetitions of an exercise;
  inputting the measured control linear acceleration and angular velocity and individual linear acceleration and angular velocity into said computer to convert to joint angle positions, velocities and accelerations data for said individual and for said at least one control person;
  segmenting said data such that each segment begins with the start of an exercise repetition and ends when the exercise repetition is finished;
and applying a Lasso analysis of the data collected to obtain said features.

BRIEF DESCRIPTION OF THE FIGURES

These and other aspects of the present invention will be apparent from the brief description of the drawings and the following detailed description in which.

DETAILED DESCRIPTION

Figure 1:
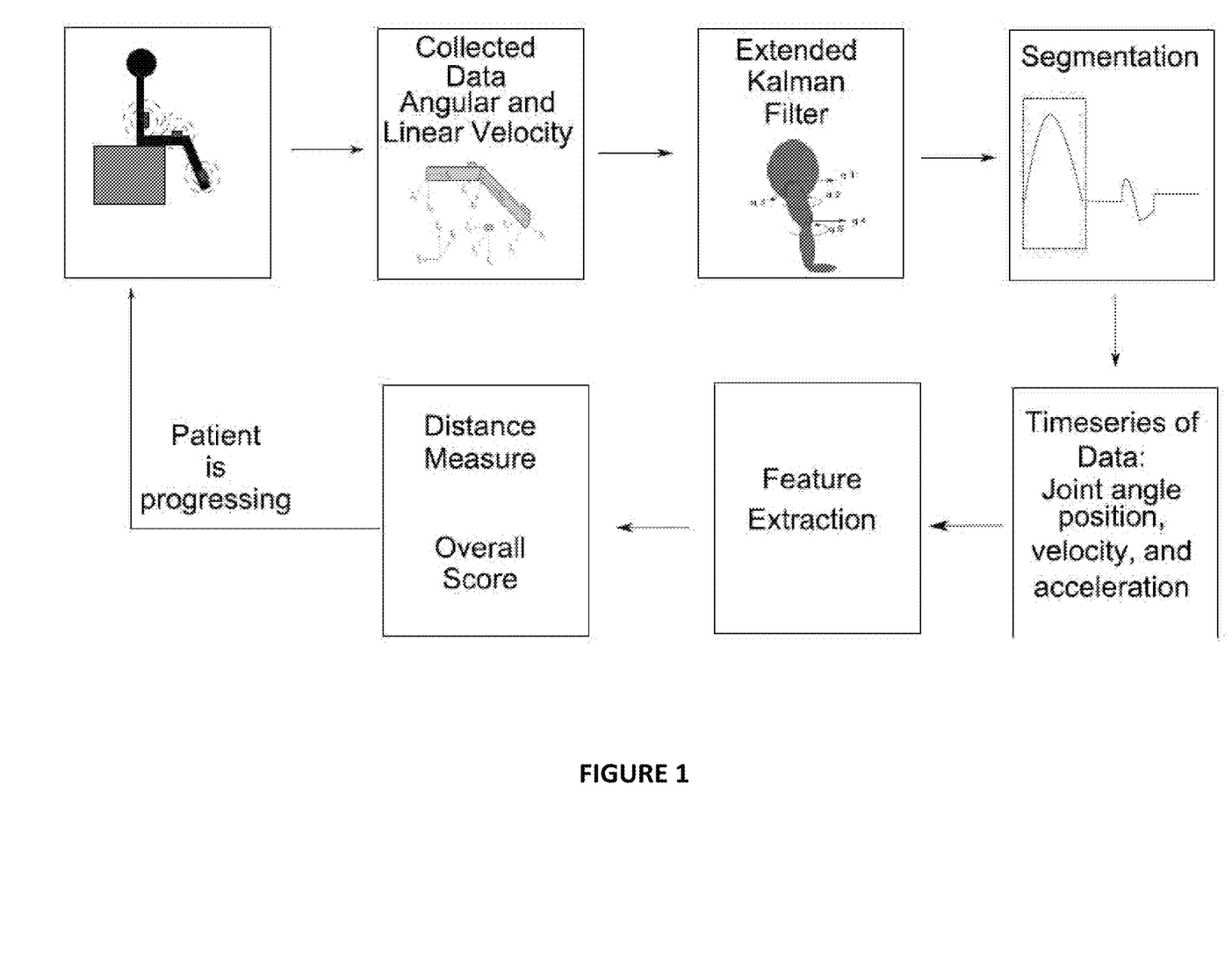
FIG. 1 is a flowchart of the overall system of an embodiment of the present invention.

An embodiment of the overall system is shown in FIG. 1, in which raw data is collected from a patient through the use of sensors. The raw data collected is then filtered and segmented to estimate the joint angles and isolate the desired movement(s) to be monitored, consisting of joint angle positions, velocities, and accelerations, and to eliminate background movement. This system not only considers a single joint in the analysis, but simultaneously all of the joints in the kinematic chain considered (e.g., leg in the case of leg rehabilitation).

The joint angle data is then segmented to extract each specific movement that is being analyzed. A segment begins with the start of an exercise repetition and ends when the exercise repetition is finished. Descriptive features are calculated for the joint angle positions, velocities, and accelerations. The data collected is then compared to data previously collected from healthy participants performing the same exercises, and the healthy population data is used as a reference.

The patient data collected is then compared to the healthy population data. The difference between the patent data and the healthy population data is referred to as the distance. Distance measures quantify the performance quality of: a) a single repetition of an exercise; b) a set of repetitions of the same exercise; and c) a set of different exercises. These measures are used to provide the patients and the physiotherapists with feedback on the patient's performance during rehabilitation.

Data can be collected through the use of robotic exoskeletons or marker based motion capture systems or wearable motion capture systems based on IMU sensors. In the case of IMU sensors, any sensor having a gyroscope and an accelerometer will collect the required data, for example a Shimmer™ sensor. Although a wired sensor will function for the purposes of this present system, it is preferable to use a wireless sensor. For example, one or more sensors connected through WiFi such as Bluetooth. A wireless system is preferable as a wired sensor may tug on the body of the wearer causing motion of the body or motion of the sensor which may impact the results of the data collected.

The data collected by the sensors is input onto a computing device. Any computing device having a processor may be used, for example, a computer, laptop, tablet, phone, or computer processor.

The sensor or sensors continuously measure all movement of the wearer. In an embodiment of the present invention, the sensors measure the angular velocity and linear acceleration, while the system estimates the joint positions, velocities and linear accelerations, as shown in FIG. 1. In an embodiment, the data collected by the sensor or sensors is converted by way of a filter, such as an extended Kalman filter (EKF). A linear filter is not used, because the relationship between the Cartesian velocities/accelerations and joint angles/velocities/accelerations is non-linear. The extended Kalman filter is used, which extends the linear Kalman filter to allow non-linear observation and state equations. This is an algorithm that uses a series of measurements observed over time, containing noise (random variations) and other inaccuracies, and produces estimates of unknown variables that tend to be more precise than those based on a single measurement alone.

The filter estimates the joint angles, velocities and accelerations, or other data, in regular intervals. It is understood that the intervals at which the algorithm estimates can be set when the sensor settings are set, for example every 30 to 50 Hertz. It is further understood that the intervals may vary beyond 30 to 50 Hz depending on the patient, the purpose of using the system, the joints being measured, etc.

The filtered data is then segmented in order to extract from the raw data collected the specific movement that is being analyzed. The segmentation of the raw data separates the data associated with the patient performing the actual movement that is being analyzed from other movements, such as stretching, shaking out the joint between exercises, stopping, walking around, etc.

The segmented data is next compared to a healthy population data using either a feature based method or a probabilistic or HMM method. The difference, or distance, between the patient's segmented data and the healthy population data is then recorded and measured against subsequent segmented data. Through comparing the distance of a patient over a period of time, patient progress can be monitored. The period of time can be during a single session, or over a period of days, months, or years.

The data collected through the use of analysing patient progress addresses the questions of how to assess one repetition of one exercise performed by a patient; how to assess multiple repetitions of one exercise performed by a patient; and how to combine the evaluations from different exercises and obtain a score that denotes the overall performance of a patient in a single session.

In an embodiment of the invention, the motion data of patients recovering from knee or hip replacement surgery is collected in the form of, for example, angular velocities and linear accelerations, from which joint angle positions, velocities and accelerations are computed using the EKF. The motion data from a healthy population performing the same set of exercises is also collected. To demonstrate the invention, the following exercises are analyzed: knee extension/flexion while seated, knee and hip extension/flexion while supine, and squat. Shimmer sensors are mounted at the knee and ankle to provide angular velocity and linear acceleration data at 128 Hz.

The data is segmented such that one single repetition of a certain exercise is a repetition time series data $\omega=[\gamma_{(1)}\gamma_{(2)} \ldots \gamma_{(T)}]$, where T is the duration of the repetition for that exercise, and $\gamma$ is a vector of joint kinematics $\gamma=[q_1 \, q_2 \ldots \dot{q}_1 \, \dot{q}_2 \ldots \ddot{q}_1 \, \ddot{q}_2 \ldots]$. Multiple repetitions of the same exercise performed in the same session are the repetition set for that exercise $\Omega=[\omega_1 \ldots \omega_n]$ where n is the number of repetitions. The set of multiple exercises performed in the same session are the session set of that session $\Gamma=[\Omega_1 \ldots \Omega_m]$ where m is the number of different exercises performed in the session.

Figure 2:
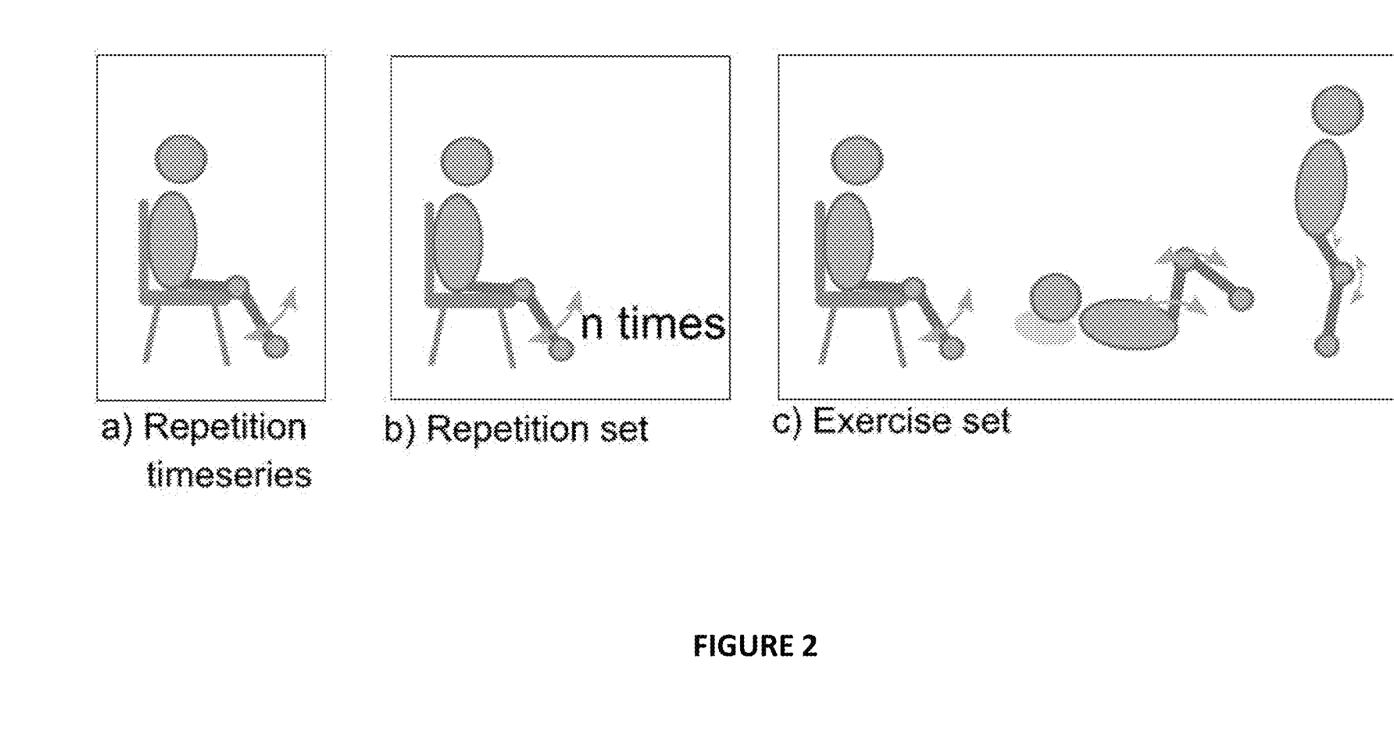
FIG. 2 is a graphical representation of the a) repetition timeseries, b) repetition set, and c) exercise set according to an embodiment of the present invention.

Two methods are described that measure the variability caused by improvement and progress throughout the rehabilitation by reference to a healthy population. In the first method, descriptive measures such as minimum, mean, or maximum are extracted from the joint angle position, velocity and acceleration time series data. The second method relies on the features extracted from a generative model for the joint angle time series. Measures $\delta$ and $\Delta$ for assessing one and multiple repetitions of one exercise are introduced based on a comparision between the healthy population and the patient. The overall score S is calculated as a function of these measures for multiple exercises in one session and is shown in FIG. 2.

Approach 1—Feature Based Approach

In the first method, the mean, minimum, maximum, skew and range of motion of joint angle positions, velocities and accelerations along with the duration of exercise for each repetition time series are considered as the feature vector.

$$v=[\text{mean}_{q_1} \text{min}_{q_1} \text{max}_{q_1} \text{skew}_{q_1} \text{rom}_{q_1} \text{mean}_{q_2} \ldots \text{duration}]$$

The feature vectors are extracted for each repetition of every exercise performed over the course of rehabilitation. These features are also extracted from the healthy population data for the same exercise. Features that most reflect the changes throughout the rehabilitation are chosen using the LASSO method from Tibshirani, R. (1996) *Regression shrinkage and selection via the lasso*. J. Royal. Statist. Soc B., Vol. 58, No. 1, pages 267-288.

The healthy data is the reference and the distance to the mean of this dataset is the measure of progress for each exercise. The results of different exercises are normalized by mean and variance of their corresponding healthy dataset. The measures are then combined to obtain an overall score for each patient's performance in a given session.

Feature Based Approach—Feature Selection

A linear model is used for feature selection, i.e., for identifying which features change during the course of treatment. For the healthy population data, a linear model is used to estimate the suitability of features to discriminate between the healthy population and patient data.

For a set of inputs $f_1, f_2, \ldots, f_n$, an output y and the following linear model:

$$\hat{y} = w_0 + w_1 f_1 + w_2 f_2 + w_3 f_3 + \ldots + w_k f_k$$

LASSO adjusts the weights $w_0, \ldots, w_k$ such that $\Sigma(\hat{y}-y)^2$ is minimized and $\Sigma_{i=0}^n w_i < t$ where $t \geq 0$ is a tuning parameter under LASSO. The second criterion drives the weights of non-informative inputs to zero. When $w_i$ becomes zero the input $f_i$ does not contribute in minimizing $\Sigma(\hat{y}-y)^2$.

The inputs $f_1, f_2, \ldots, f_n$ are the features of the repetition time series data and the output y is the corresponding session number. The session numbers are normalized between 0 and 1, such that 0 corresponds to a patient's first session, and 1 corresponds to a patient's last session. The session numbers are a linear function of suitable features that allows one to find the features that are changed most with patients' progress through the sessions.

Healthy population data in this regression is also considered. Label y for the healthy population is considered to be 100 times larger than patients' last session. Introducing this outlier forces the regression to be in the direction of the healthy population data and helps detecting the features that not only change with the progress of the patients but also separate the healthy population from patients.

The value of y for the healthy population directly affects the value of weights but the chosen features are not changed as long as the y value is sufficiently large. When the weight $w_i$ becomes zero it is interpreted that feature $f_i$ is uninformative and therefore is removed from the feature vector. The top features chosen by the LASSO technique are used for the subsequent analysis.

Feature Based Approach—Measure of Performance for Repetition Timeseries

To obtain a measurement for the performance of one exercise, the feature vectors are extracted for the patient ($V_P$) and healthy population ($V_H$) data as explained above.

$$V'_H = V_H(\text{top}_{features})$$

$$V'_P = V_P(\text{top}_{features})$$

Among the features chosen by LASSO, the ones with higher variance in the healthy population are more informative. Therefore more weight is given to the more variant features in defining the distance measure. To evaluate each repetition the distance between the patient repetition and the healthy population data is found using the following equations:

$$\mu_H = \text{mean}(V'_H)$$

$$\Sigma_H = \text{diag}(\text{std}(V'_H))$$

$$\delta_i = (V'_{Pi} - \mu_H)^T \Sigma_H (V'_{Pi} - \mu_H) \text{-Equation (1)}$$

Where $V'_H$ is the healthy population top feature vector, $V'_{Pi}$ is the patients' top feature vector for the ith repetition timeseries, $\mu_H$ is the mean of the healthy populations' top feature vector, $\Sigma_H$ is the diagonal matrix of standard deviations for the healthy population top feature vector, $\delta_i$ is the distance between one repetition of the exercise performed and the healthy group's performance. As patients improve they get closer to the healthy data and therefore a decrease in the value of $\delta$ over the course of rehabilitation indicates improvement.

Feature Based Approach—Measure of Performance for Multiple Repetitions of the Same Exercise The median of the distance measures ($\delta$) calculated for one exercise over the session is considered as the overall distance measure for the repetition set of that exercise:

$$\Delta_\Omega = \text{median}(\delta_\Omega)$$

Where $\Delta_\Omega$ is the overall performance of one exercise in one session. and $\delta_\Omega$ is the vector of distance measures calculated for every repetition timeseries data $\omega_i$ in the repetition set $\Omega$.

Feature Based Approach—Measure of Performance for a Combination of Exercises

The distance obtained in measuring the performance for multiple repetitions of the same exercise only describes the patients' performance for one exercise (i.e. $\Omega_j$) in each session. There are multiple exercises performed in each physiotherapy session (i.e. $\Gamma$) that need to be considered together for overall patient progress assessment. Quality and quantity are the two factors that affect scoring an exercise. The variance of distance measures calculated for the healthy population is used as a measure of exercise difficulty. The compensation strategies performed by the healthy population have larger variances when the exercise is more difficult and the distance measures of the healthy population have larger variance for more difficult exercises.

The distance measures ($\delta$) are calculated for every repetition timeseries of the healthy population according to Equation 1 and are considered as the comparison reference.

The healthy population distance measure vector $\delta_{Hj}$ is the vector of the distance measure calculated for every repetition timeseries of exercise $\Omega_j$ in the healthy population data. The patient distance measures ($\Delta_{Pj}$) are calculated for the repetition set of every exercise $\Omega_j$ in the exercise set $\Gamma$. The mean and standard deviation of the healthy population distance measure vector $\delta_{Hj}$ are considered as the measure of exercise difficulty and are calculated using the following equations $$\mu \delta_{Hj} = \text{mean}(\delta_{Hj})$$

$$\sigma \delta_{Hj} = \text{diag}(\text{std}(\delta_{Hj}))$$

where $\mu \delta_{Hj}$ is the mean of the healthy population distance measure vector $\delta_{Hj}$ and $\sigma \delta_{Hj}$ is the standard deviation of the healthy population distance measure vector $\delta_{Hj}$.

The measure of quality for a repetition set of an exercise j performed by the patient is:

$$Q_j = \frac{(\Delta_{Pj} \mu_{\delta Hj})}{\sigma^2_{\delta Hj}}, \quad \text{Equation (2)}$$

where $\Delta_{Pj}$ is the patient's distance measure for the repetition set of exercise j. A perfect performance over any repetition set $\Omega$ results in a value of zero for the overall distance measure ($\Delta_\Omega = 0$). The overall score for the patient in a specific session is calculated as the difference between the norm of the score resulting from a perfect performance and the norm of the weighted quality measures. The quality measure $Q_j$ of an exercise j is weighted by its number of repetitions. The score of the patient for a given session is calculated using the following equation $$S = \sqrt{\sum_{\Omega \in \Gamma} \left( \frac{n_\Omega}{\sum_{\Omega \in \Gamma} n_\Omega} \frac{\mu_{d_{H_\Omega}}}{\sigma^2_{d_{H_\Omega}}} \right)^2} - \sqrt{\sum_{\Omega \in \Gamma} \left( \frac{n_\Omega}{\sum_{\Omega \in \Gamma} n_\Omega} Q_\Omega \right)^2} \quad \text{Equation (3)}$$

where $\Gamma$ is the exercise set, $\Omega$ is an exercise in the $\Gamma$, $n_\Omega$ is the number of repetitions for exercise $\Omega$, and $Q_\Omega$ is the quality measure calculated for exercise $\Omega$ using Equation 2. The score S is formulated such that performing a difficult exercise in a session would improve a patient's score. Furthermore, exercises with more repetitions in one session are the main focus of that session and therefore, the quality measures Q are weighted by the number of repetitions for each exercise. The score S is defined as the difference between a perfect weighted quality measure and the patient's weighted quality measure hence progress results in smaller values for this measure.

The healthy population's distance values are often small and have a small variance compared to patient data. In some cases the healthy population's distance measure variance $\sigma \delta_{H_j}$ becomes smaller than 1. In Equation 2, we want to normalize the quality measure according to the healthy population performance. To avoid dividing the quality measure with a value less than 1, all the $\delta$ values are scaled uniformly for the healthy population and patient data such that all variance values of the healthy population's distance measures become greater than 1. The algorithm flexibility in defining any exercise set allows us to calculate the overall score for any arbitrary set of exercises.

Approach 2—HMM Approach

In the second method, the Hidden Markov Model (HMM) based approach relies on features extracted from HMMs modeling the joint angle timeseries. HMMs are trained on the repetition set of the healthy and unhealthy populations separately. The HMM is described in L. R. Rabiner, "A tutorial on hidden markov models and selected applications in speech recognition", *Proceedings of the IEEE*, vol. 77, no. 2, pp. 257-286, 1989.

The HMMs are learned for each member of the healthy population separately. For the data of each patient, individual HMMs are learned for every repetition set of each session (some sessions include more than one repetition set of an exercise). The observations of the HMMs are the position, velocity, and acceleration of the joint angles, and the mean and variance of the observation distributions in each state are considered as the feature vector.

LASSO feature selection is used to choose the most informative features, similar to the approach described in Feature Selection of the Feature Based Approach 1. The distance measure is calculated using Equation 1. The quality measure Q is calculated using Equation 2 and the overall performance score S is calculated using Equation 3.

HMM Approach—Feature Selection

HMMs are trained for the repetition sets of each exercise for the healthy population and the patient data. The observations are the joint angle positions, velocities, and accelerations. Each repetition set is modelled using a 3 state, left to right model. States 1, 2, and 3 correspond to the stages: attempt to reach the desired posture, reaching the desired posture and pausing, and returning to the starting posture.

The feature vector includes the parameters of the observation distributions, which are the means and variances of joint angle positions, velocities and accelerations for the three states $$v = \begin{bmatrix} \mu_{state_{1_{q_1}}} & \sigma_{state_{1_{q_1}}} & \mu_{state_{2_{q_1}}} & \cdots & \mu_{state_{3_{\ddot{q}_5}}} & \sigma_{state_{3_{\ddot{q}_5}}} \end{bmatrix}$$

The feature selection is performed using LASSO as described in the Feature Based Approach.

HMM Approach—Measure of Performance for a Repetition Timeseries

An advantage of the HMM is that it can be trained using several timeseries and that it represents the most likely timeseries. For this reason, training HMMs for each repetition timeseries is not necessary to assess the performance for an exercise set or to assess an overall score.

HMM Approach—Measure of Performance for Multiple Repetitions of the Same Exercise Of the top features chosen by LASSO, those that are highly variant in the healthy population indicate the rehabilitation process better. Therefore, distance measures are calculated as in the Feature Based Approach. The ten features chosen by LASSO are chosen as the top features. The distance measure $\Delta_{HMM}$ for a repetition set is obtained using the HMM-based feature vectors and Equation 1.

HMM Approach—Measure of Performance for a Combination of Exercises

Based on $\Delta_{HMM}$ the procedure follows the Feature Based Approach. The quality measure is defined by Equation 2 and is based on the patient's distance measure $\Delta_{HMM}$ for a repetition set. The overall score $S_{HMM}$ of a session is obtained using Equation 3.

In this example, motion data is collected using Shimmer sensors mounted at the knee and ankle providing angular velocity and linear acceleration data (128 HZ). Position q, velocity $\dot{q}$ and acceleration $\ddot{q}$ of five joint angles consisting of knee flexion, knee rotation, hip flexion, hip abduction, and hip rotation are estimated from the sensor data based on a kinematic model and an Extended Kalman Filter described at J. F. Lin and D. Kulic, "Human pose recovery using wireless inertial measurement units", *Physiological measurement*, vol. 33, no. 12, p. 2099 (2012). The joint angle variables are denoted as $$\gamma = [q_1 \dot{q}_1 \ddot{q}_1, \ldots, q_5 \dot{q}_5 \ddot{q}_5]$$

Results Using Feature Based Approach 1

Figure 3:
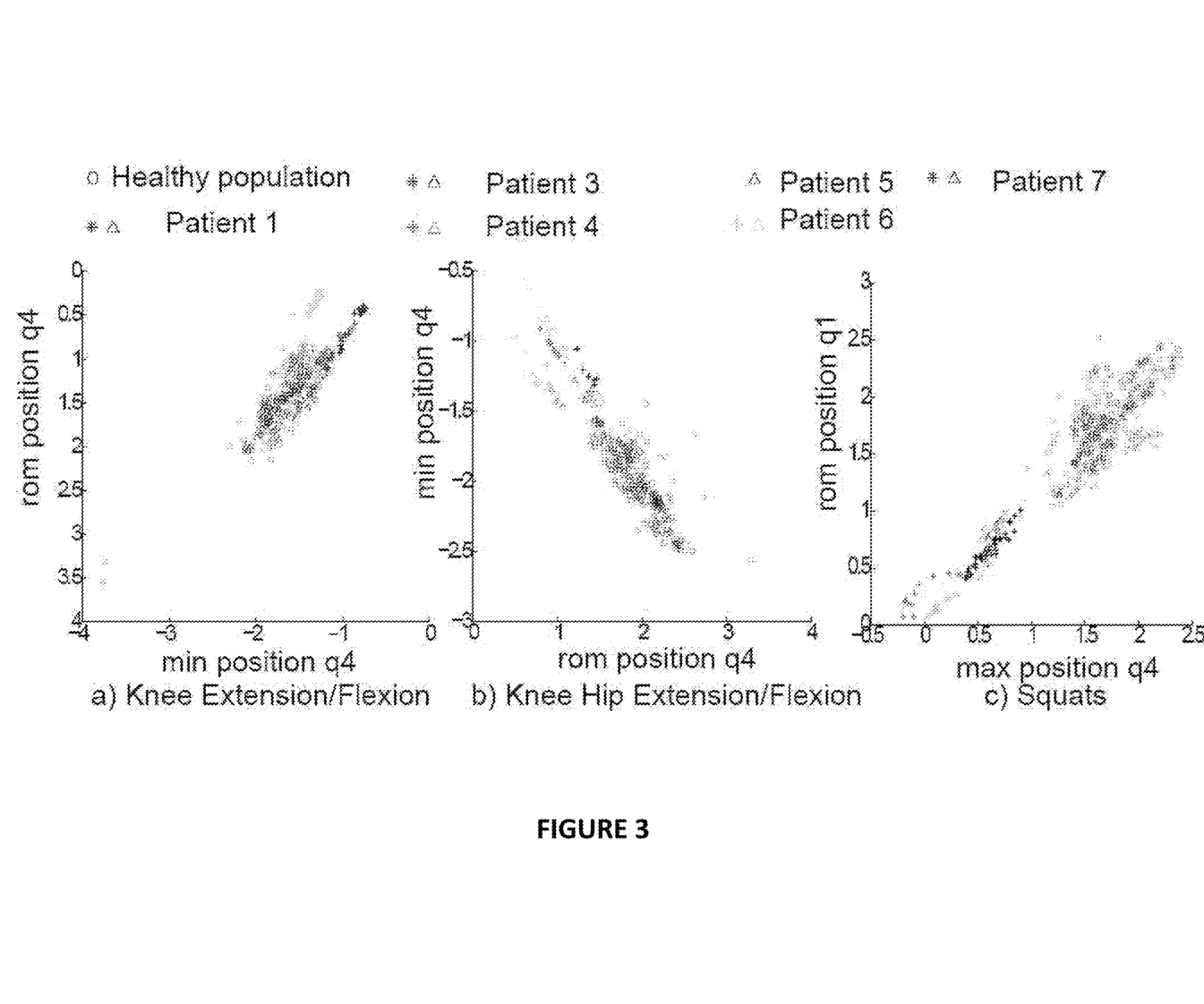
FIG. 3 are charts plotting patient and healthy population data for the most informative features for six patients for a) knee extension/flexion; b) knee hip extension/flexion and c) squats, in an embodiment of the present invention.

The LASSO technique described above is used for feature selection. FIG. 3 shows that patient data and healthy population data are clearly separable for the most informative features. The star indicates the first day the patients have performed the exercises and the triangle indicates the last day the patients have performed the exercises (only 1 session available for patient 5). q1 is the joint angle corresponding to hip extension and q4 is the joint angle corresponding to knee extension. FIG. 3 shows the distribution of the repetition timeseries of the healthy population and the training subset of the patient data over the two features selected by LASSO that have the largest variance in the healthy population. The clusters of the healthy population data and the patient data are clearly separable. Furthermore, FIG. 3 shows that a patient's progress is in the direction of the variance of the healthy population data and moves towards the mean of the healthy population as the patients improve their performance during rehabilitation. When patient data is not available for training, features may be selected by largest variance within the healthy population data.

Figure 4:
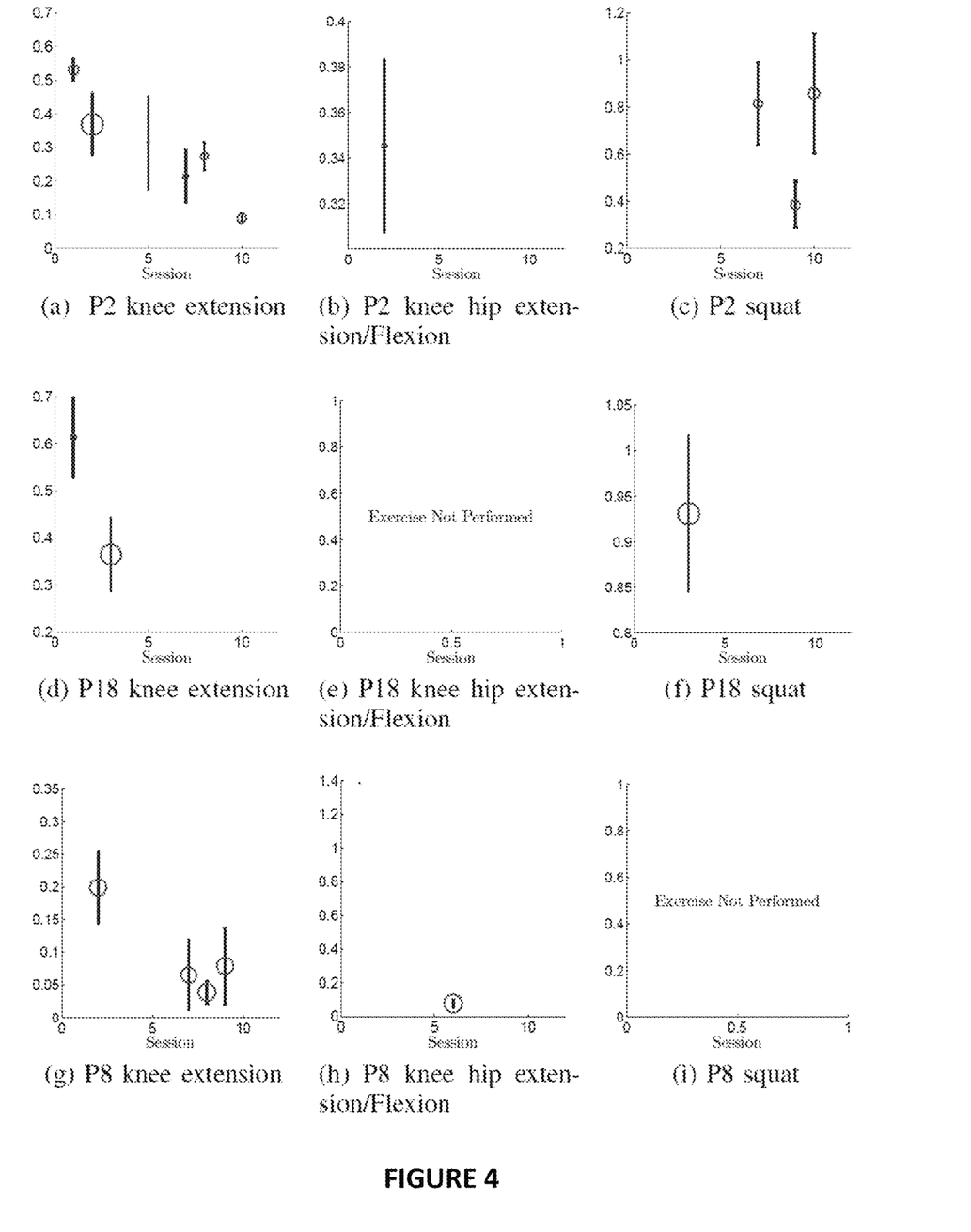
FIG. 4 shows the results of distance measure analysis using the feature-based approach for three patients for the exercises of knee extension, knee hip extension/flexion and squats, in an embodiment of the present invention.

The distance measure $\Delta$ provides information about the progress for each repetition set $\Omega$ through the rehabilitation. When patients improve, the distance measure decreases towards zero. FIG. 4 shows the results for the distance measure δ calculated using the feature-based approach, shown for three exercises. The circle illustrates the median of the distance measures (i.e. Δ) in each session and the bar depicts the variance of the distance measures δ in one session. The size of the circle indicates the number of repetitions available in each repetition set. FIG. 4 shows the calculated distance measure Δ and the distribution of δ for the 3 example patients. The exercise regimen is specific to each patient. The exercises are performed in a subset of the sessions, e.g., patient 2 performs knee extensions in session 1, 2, 7, 8 and 10. Furthermore factors such as pain, fatigue, psychological status, and environmental conditions contribute to patients' performance and it cannot be expected that the patient progress increases monotonically.

Figure 5:
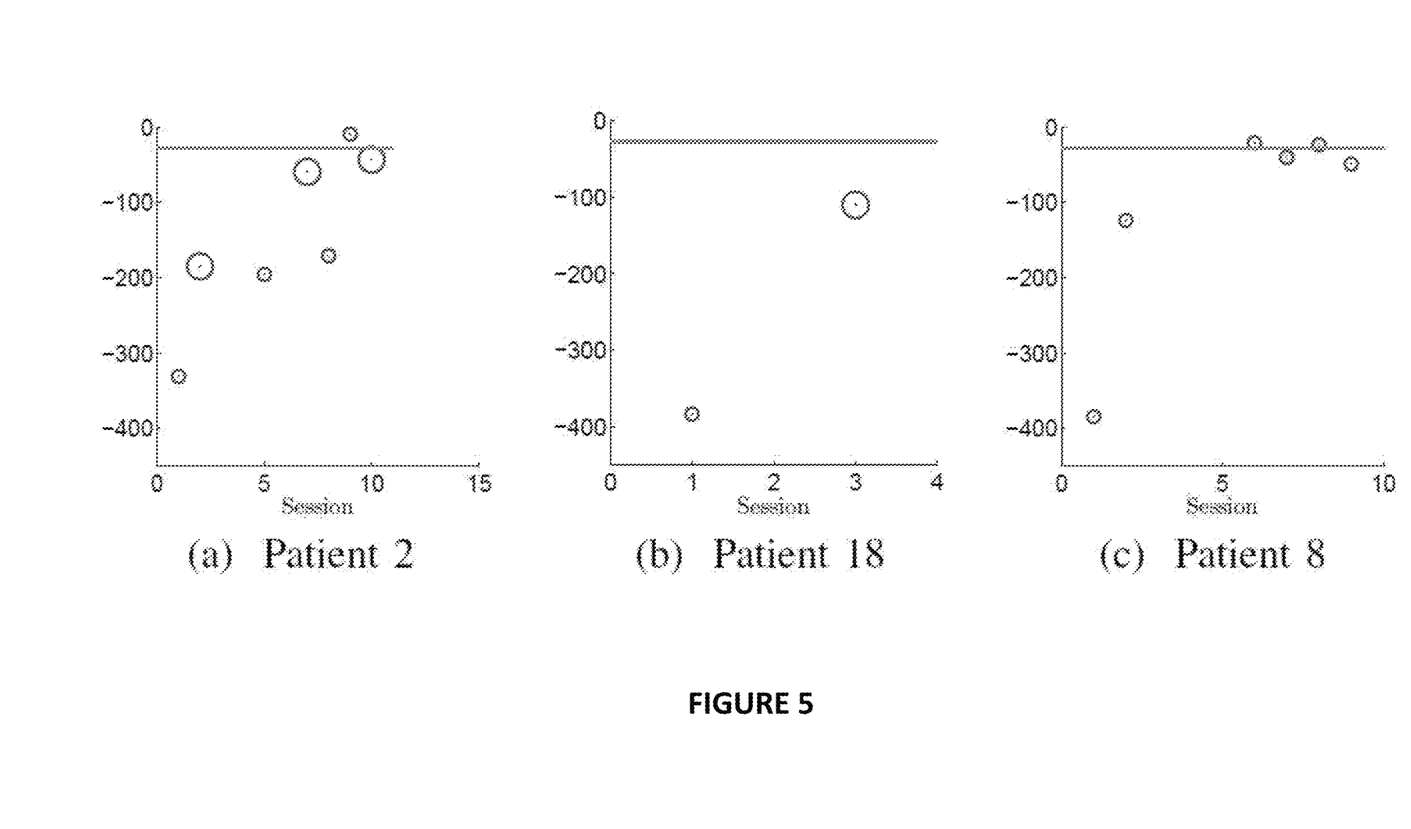
FIG. 5 shows the results of overall score using a feature-based approach for an exercise set, combining individual distance measures of knee extension, knee-hip extension and squat for three patients a), b), c), in an embodiment of the present invention.

For all three patients an overall improvement over the course of the physiotherapy treatment can be observed. Some patients show rapid progress and are discharged early, e.g., patient 18 (in FIG. 4d). The distance measure for a repetition set is more reliable when the number of repetitions available for that exercise is larger. The feature-based approach generalizes to unseen patient data, e.g., the data of patients 8 and 18 was not used for the feature selection and the distance measure Δ shows the patient's progress throughout the rehabilitation as demonstrated in FIG. 4g. The quality measure Q and the overall score S for each session are obtained according to Equations 2 and 3 using the overall distance measure Δ calculated for every repetition set of each session. As patients improve, the overall score increases from negative values towards zero. FIG. 5 shows an overall score S calculated for an exercise set, combining individual distance measures Δ of knee extension, knee-hip extension, and squat. The size of the marker indicates the number of exercises available in each session. The top line shows the best score of the patients in their last physiotherapy session.

FIG. 5 shows the score measures for each patient. It can be seen from the figures that the trend of the score shows progress but there are some inconsistencies in patient 2, session 8 (in FIG. 5a). These inconsistencies are caused by a small number of performed exercise repetitions.

Due to differences in health status, the exercise regimen of each session is different from one patient to the other. Among the three exercises chosen for analysis, there are sessions where only one of these exercises is performed and therefore the score is based solely on the performance quality of that single exercise. This results in inconsistencies in the improvement trend of the score measure since a poor performance in one exercise is not an accurate measure of the patient's overall status. The score measure estimates the patient's overall status more accurately when more exercise data from each session is available.

For patient 18, who had a fast recovery and was discharged after only 3 sessions, the score is able to capture the rapid trend of progress in FIG. 5b. As can be seen in FIG. 3, the top features capturing patient progress are highly variant in the healthy population. If patient data is unavailable, the feature-based approach can be performed using only the most variant features in the healthy population. Since feature selection is not performed on patient population data, variabilities due to initial posture may be selected as highly variant features among the healthy population. To avoid this, features obtained from joint angle positions were removed from the considered feature vector. The feature vector for each repetition timeseries data becomes $$v = [\mu_{q_1} \min_{q_1} \max_{q_1} skew_{q_1} rom_{q_1} \mu_{q_2} \ldots duration]$$

Figure 8:
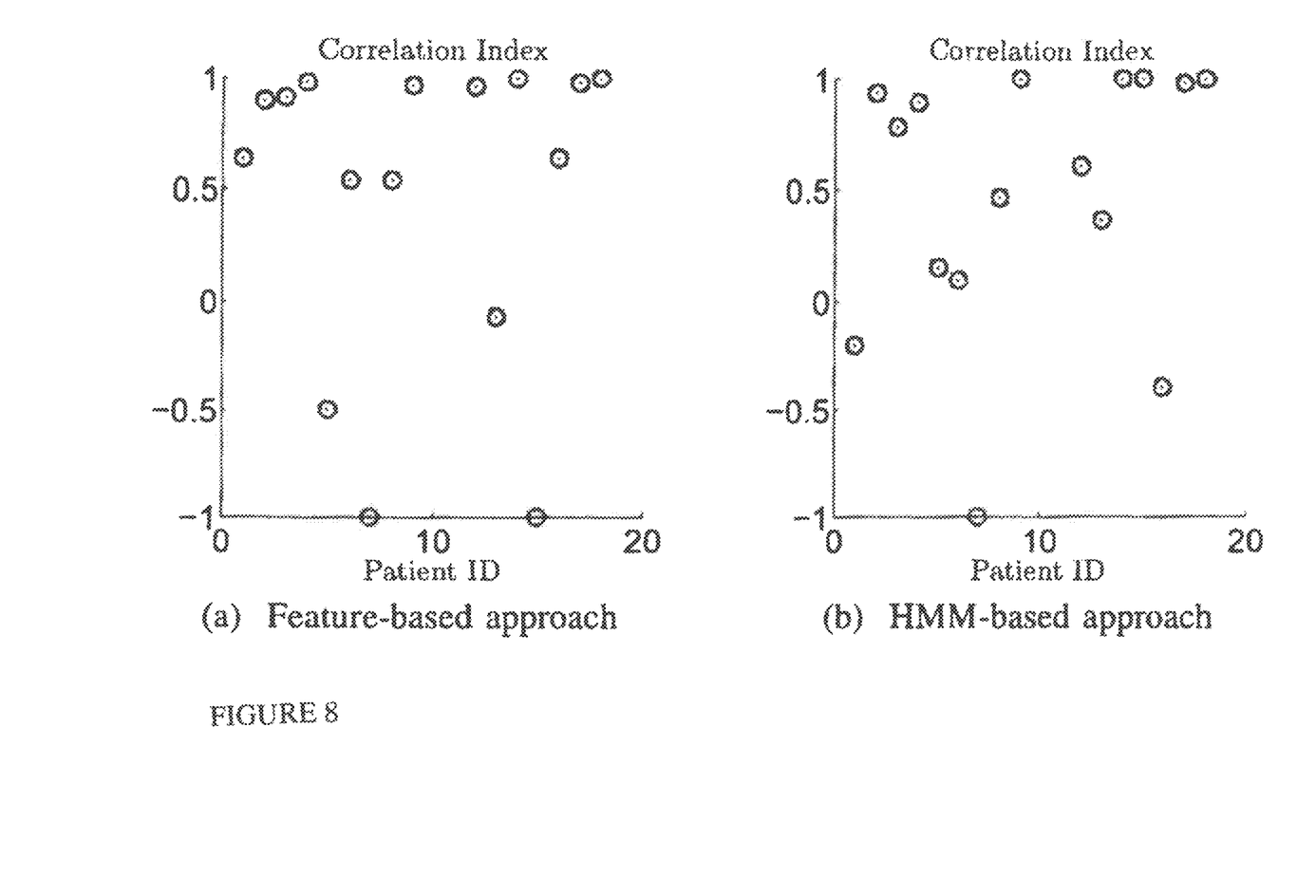
FIG. 8 is the correlation index for a) feature-based approach and b) HMM-based approach.

Among the first fifteen most variant features in the healthy population, those that correlate least with each other (less than 0.5) are chosen as the top features. The distance measure is calculated for each repetition timeseries using Equation 1. The median of the distance measures δ calculated for the repetition timeseries is considered as the overall distance measure Δ for a repetition set. The quality measures and the overall score of each session are calculated using Equations 2 and 3. FIG. 8 shows the correlation index between approaches with feature selection on healthy and unhealthy data and approaches with feature selection only on healthy data are for most patients over 0.65.

FIG. 8a shows the correlation between the overall score from the feature-based approach when using healthy and patient population data for feature selection and when using only healthy population data for feature selection.

As can be seen in FIG. 8a, the results correlate highly (over 0.65) for most patients. Even though feature selection based only on healthy population data does not take compensation strategies specific to the patient population into account, the extension using only healthy population data for feature selection can detect patient progress. When the overall performance of a patient is constantly high (patient 7 and 15) or low (patient 5) over the course of the rehabilitation, changes in the scores are small. In these cases, the correlation index can be low, because the two techniques differ when assessing small changes in performance.

Results Using HMM-Based Approach

Figure 6:
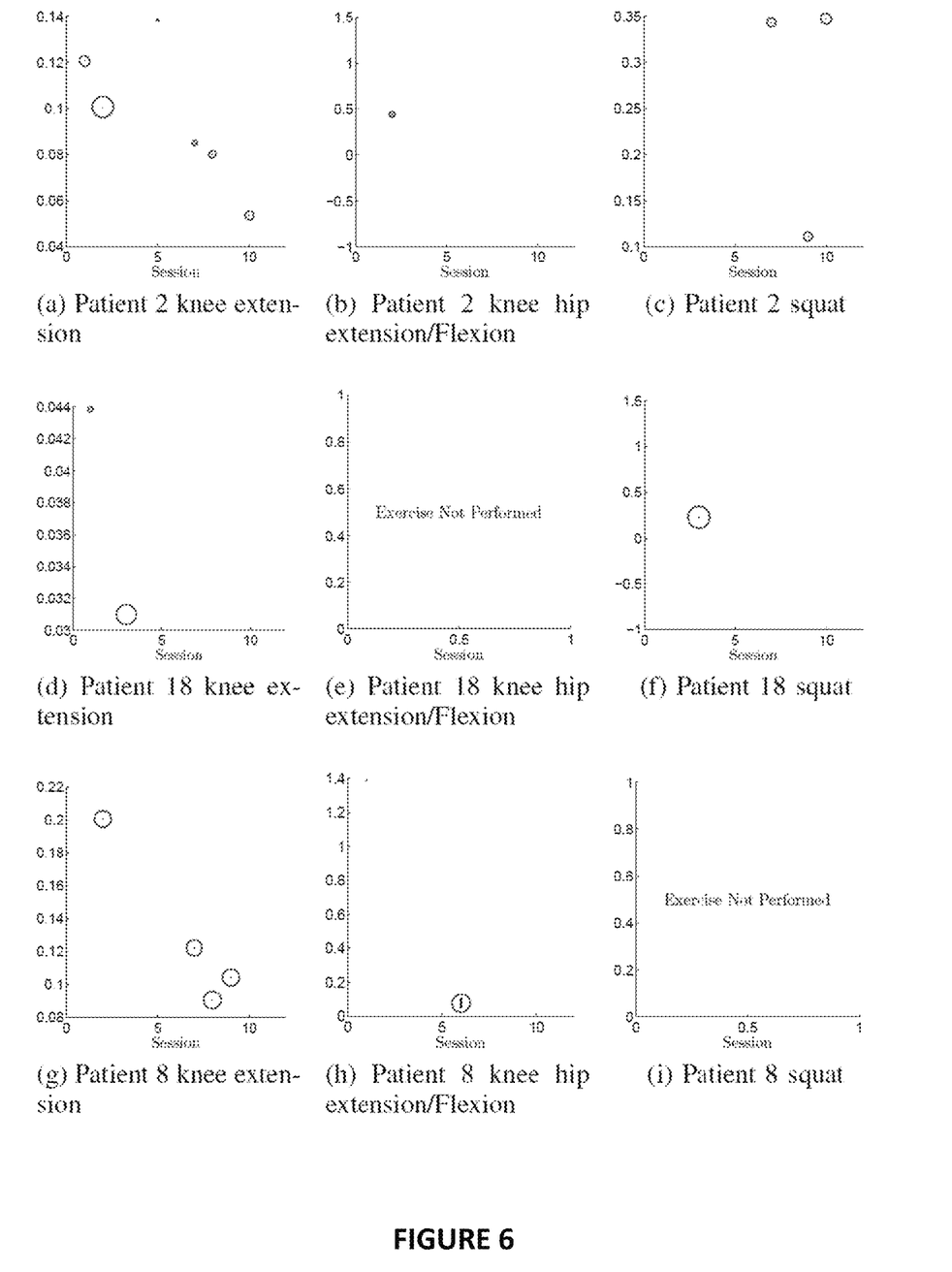
FIG. 6 shows the results of distance measure analysis using the HMM approach for three patients for the exercises of knee extension, knee hip extension/flexion and squats, in an embodiment of the present invention.

HMMs are trained for the down sampled repetition sets for every healthy subject and every session of each patient. The feature vectors are obtained from the states of the HMMs and most informative features are selected. The distance measure Δ is calculated for each repetition set using Equation 1. As patients improve the distance measure decreases towards zero. FIG. 6 shows the HMM-based distance measure $\Delta_{HMM}$ which shows the trend in progress over the sessions, here illustrated for patients 2, 8, and 18. The marker size indicates the number of repetitions available in the repetition set. FIG. 6 shows the results of calculations for the overall distance measure Δ. The features chosen by LASSO capture the progress in unseen data, e.g., shown for patient 8 in FIG. 6g.

Figure 7:
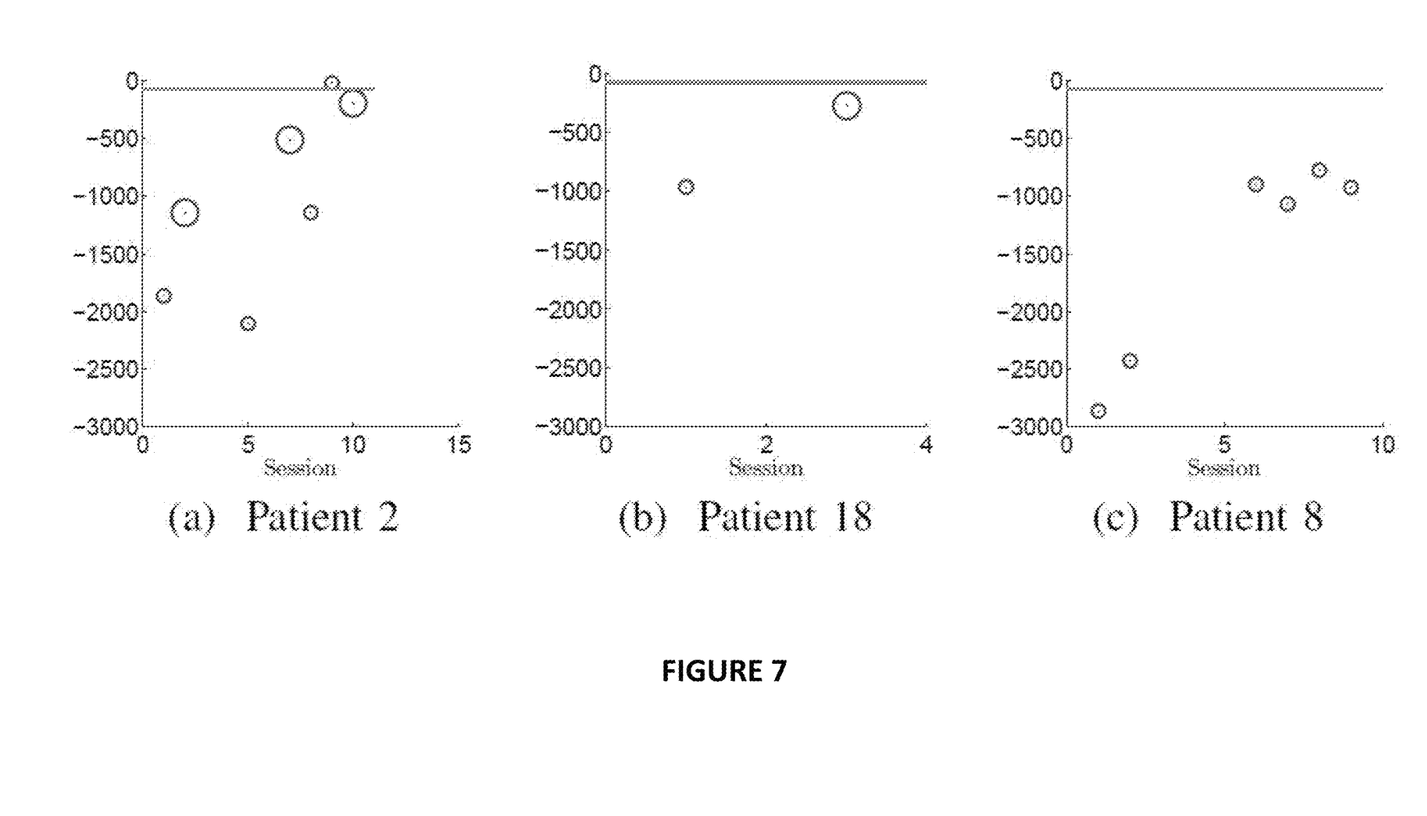
FIG. 7 shows the results of overall score using the HMM approach for an exercise set, combining individual distance measures of knee extension, knee-hip extension and squat for three patients a), b), c), in an embodiment of the present invention.

The quality measure Q of each exercise in one session is calculated using Equation 2 and the overall score S for the exercise set performed in each session is calculated using Equation 3. The overall score increases from negative values towards zero as the patients improve. FIG. 7 shows the overall score $S_{HMM}$ which shows the trend of progress during rehabilitation. The marker size indicates the number of exercises available for each session. The top line shows the best score of the patients in their last session of performing the three exercises. FIG. 7 shows the scores $S_{HMM}$ for each patient. The scores show an overall trend of improvement for most patients. As before, the reliability of the score measure depends on the number of available exercises, i.e., outliers are usually observed when only one exercise is available to calculate the score. The features chosen by LASSO generalize well to the unseen data e.g., patient 8 whose trend of improvement is captured by the approach (in FIG. 7c).

The approach captures the rapid improvement of patient 18 (in FIG. 7b), who is discharged earlier than other patients. Healthy population data is sufficient for feature selection for the HMM-based approach.

Among the first fifteen most variant features in the healthy population, those that correlate least with each other (less than 0.5) are chosen as the top features. The distance measure $\Delta_{HMM}$ for each repetition set is calculated using Equation 1. The quality measure $Q_{HMM}$ for each repetition set is calculated using Equation 2 and the overall score $S_{HMM}$ is calculated for each patient and each session using Equation 3.

The correlation between the overall score using healthy and patient population data for feature selection and using only healthy population data for feature selection is above 0.65 for most patients (see FIG. 8b). Negative correlation indices are observed when the changes in a patient's progress are small.

For both the feature-based and the HMM-based approach, the distance measure $\Delta$ for a repetition set and the overall score S for an exercise set assess patient progress. The feature-based approach is faster to compute whereas the HMM-based approach provides details about each stage of a motion.

Since the exercise regimen differs between patients and large variability is observed in the patient population, it is difficult to use only patient data for learning a model which estimates patient progress and generalizes to new patients. The proposed approaches achieve generalization to new patients by including healthy population data as reference. Feature selection is based on patient and healthy population data and an extension is evaluated using only healthy population data for feature selection. This extension is beneficial when including new exercises into the exercise regimen without having access to patient data.

Furthermore the score measure formulations can be applied to any set of exercises as long as the corresponding healthy population data is available. This flexibility enables the physiotherapist to include patient specific or novel exercises requiring only a healthy reference set. The score measure is formulated in a way to handle individual exercise regimens and a variable number and type of exercises.

Quantified and continuous measure of performance can be beneficial for monitoring patient progress during the course of physiotherapy rehabilitation. This work introduces two approaches, feature-based and HMM-based, for capturing the continuous change in patient data. A distance measure is introduced as a measure of performance for a repetition timeseries and repetition set. The overall score is then calculated for the exercise set in each session and captures the overall performance of the patient. The proposed approach can be trained based on a subset of patient data and healthy population data, or using healthy population data alone, unlike most classifier methods. The two approaches of the present invention are evaluated on data of exercises commonly performed after hip or knee replacement surgery. The results show that the two approaches are able to track patient progress over the course of treatment.

This invention has applications other than rehabilitation, for example, it is used to measure progress (improvement in performance) during sports training, or during motion analysis/intervention/training for improving ergonomics in the workplace (avoiding workplace injuries).

The present invention when utilized for individuals measuring improvement in performance (e.g. for an athlete) or correction in performance (e.g. for an assembly line worker to avoid strain or injury), uses a comparison from a control person or control population.

The present invention utilizes software and computer processing to collect, carry out the analysis and provide results. The distance and score results can be displayed in a manner which aids in comprehension for the individual or for a therapist such as graphical visualization.

While embodiments of the invention have been described in the detailed description, the scope of the claims should not be limited by the preferred embodiments set forth in the examples, but should be given the broadest interpretation consistent with the description as a whole.

What is claimed is:

1. A method for analysing an individual's motion through a computer programmed to process information, comprising the steps of:

measuring control linear acceleration and angular velocity, using sensors on at least one control person performing a set of repetitions of an exercise or movement;

measuring individual linear acceleration and angular velocity, using sensors on said individual performing a set of repetitions of an exercise or movement;

inputting the measured control linear acceleration and angular velocity and individual linear acceleration and angular velocity into said computer to convert to joint angle positions, velocities and accelerations data for said individual and for said at least one control person;

segmenting said data such that each segment begins with a start of an exercise or movement repetition and ends when the repetition is finished;

extracting feature vectors from said data such that:
 a. a control feature vector is $V'_H=V_H(top_{features})$ and an individual's feature vector is $V'_p=V_p(top_{features})$ and said top features are a subset of features calculated based on said data that differentiate the individual from the at least one control person, and
 b. when a progression of data is available, identify and select informative features which are indicative of that progression to be used in said feature vectors and disregard uninformative features which are not indicative of that progression;

calculating a mean of the at least one control person's feature vector such that $\mu_H=\text{mean}(V'_H)$;

calculating a diagonal matrix of standard deviations for the at least one control person's feature vector, such that $\Sigma_H=\text{diag}(\text{std}(V'_H))$;

and calculating a distance between one repetition of the exercise or movement performed by said individual and the at least one control person's performance using $\delta_i=(V'_{Pi}-\mu_H)^T\Sigma_h(V'_{Pi}-\mu_H)$.

2. A method for measuring quality of a repetition set of said exercise or movement in claim 1, wherein $$Q_j=(\Delta_{Pj}-\mu_{\delta Hj}),$$

$$\sigma^2_{\delta Hj}$$

and j is said exercise or movement, $\Delta_{Pj}$ is the individual's said distance measure for the repetition set of said exercise or movement, $\mu_{\delta Hj}$, is the mean of the at least one control person's distance measure vector $\delta_{Hj}$, and $\sigma_{\delta Hj}$ is the standard deviation of the at least one control person's distance measure vector $\delta_{Hj}$.

3. A method for measuring the score for said individual in claim 2 for a set of more than one of said exercises or movements j wherein the score is $$S = \sqrt{\sum_{\Omega\in\Gamma}\left(\frac{n_\Omega}{\sum_{\Omega\in\Gamma} n_\Omega}\frac{\mu_{d_{H_\Omega}}}{\sigma^2_{d_{H_\Omega}}}\right)^2} - \sqrt{\sum_{\Omega\in\Gamma}\left(\frac{n_\Omega}{\sum_{\Omega\in\Gamma} n_\Omega}Q_\Omega\right)^2}$$

where Γ is said set of exercises or movements, Ω is an exercise or movement in the Γ, $n_\Omega$ is the number of repetitions for exercise Ω, and $Q_\Omega$ is said quality measure of claim 2 calculated for exercise or movement Ω.

4. The method in claim 1 further comprises the step of:
applying a LASSO analysis of the data collected to obtain said features, by formulating the feature selection problem as a linear regression, with a line extending from the individual to the control data.

\* \* \* \* \*